US012788254B2

(12) United States Patent
Haga

(10) Patent No.: US 12,788,254 B2
(45) Date of Patent: Nov. 10, 2026

(54) DETECTION DEVICE

(71) Applicant: Magnolia White Corporation, Tokyo (JP)

(72) Inventor: Yuta Haga, Tokyo (JP)

(73) Assignee: Magnolia White Corporation, Tokyo (JP)

( * ) Notice: Subject to any disclaimer, the term of this patent is extended or adjusted under 35 U.S.C. 154(b) by 17 days.

(21) Appl. No.: 19/007,956

(22) Filed: Jan. 2, 2025

(65) Prior Publication Data

US 2025/0134384 A1 May 1, 2025

Related U.S. Application Data

(63) Continuation of application No. PCT/JP2023/023173, filed on Jun. 22, 2023.

(30) Foreign Application Priority Data

Jul. 8, 2022 (JP) ................................ 2022-110296

(51) Int. Cl.
*A61B 5/00* (2006.01)

(52) U.S. Cl.
CPC .... *A61B 5/0077* (2013.01); *A61B 2562/0238* (2013.01); *A61B 2562/185* (2013.01)

(58) Field of Classification Search
CPC ............. H10F 55/00; A61B 2562/0238; A61B 2562/185; A61B 5/0077; A61B 5/14535; A61B 5/14552; A61B 5/6826
See application file for complete search history.

(56) References Cited

U.S. PATENT DOCUMENTS

| | | | | |
|---|---|---|---|---|
| 2008/0074401 A1 | 3/2008 | Chung et al. | | |
| 2017/0164878 A1* | 6/2017 | Connor | ............. | A61B 5/14532 |
| 2020/0151480 A1 | 5/2020 | Min | | |
| 2020/0367827 A1 | 11/2020 | Min et al. | | |

(Continued)

FOREIGN PATENT DOCUMENTS

| | | |
|---|---|---|
| JP | 2008-083675 A | 4/2008 |
| JP | 2009-254523 A | 11/2009 |
| JP | 2010-049479 A | 3/2010 |

(Continued)

OTHER PUBLICATIONS

Office Action issued in corresponding Japanese Patent Application No. 2024-532026, mailed Aug. 5, 2025 and English translation of same. 6 pages.

(Continued)

*Primary Examiner* — Mark D Remaly
(74) *Attorney, Agent, or Firm* — K&L Gates LLP

(57) ABSTRACT

According to an aspect, a detection device includes: a light source; a plurality of optical sensors that are arranged so as to be capable of receiving light of the light source and have light-receiving areas different in size; a detection circuit that is electrically coupled to each of the optical sensors and configured to detect waveform data that allows an amount of received light of each of the optical sensors to be identified; and a control circuit configured to select at least one piece of the waveform data having waveform amplitude that satisfies a selection condition from a plurality of pieces of the waveform data detected by the optical sensors.

13 Claims, 12 Drawing Sheets

(56) References Cited

U.S. PATENT DOCUMENTS

| | | | |
|---|---|---|---|
| 2021/0287025 | A1 | 9/2021 | Min |

FOREIGN PATENT DOCUMENTS

| | | | |
|---|---|---|---|
| JP | 2018-105698 | A | 7/2018 |
| JP | 2020-529695 | A | 10/2020 |
| JP | 2021-135227 | A | 9/2021 |
| JP | 2022-041267 | A | 3/2022 |

OTHER PUBLICATIONS

International Search Report issued in International Patent Application No. PCT/JP2023/023173 on Sep. 5, 2023 and English translation of same. 6 pages.

* cited by examiner

DETECTION DEVICE

CROSS-REFERENCE TO RELATED APPLICATION

This application claims the benefit of priority from Japanese Patent Application No. 2022-110296 filed on Jul. 8, 2022 and International Patent Application No. PCT/JP2023/023173 filed on Jun. 22, 2023, the entire contents of which are incorporated herein by reference.

BACKGROUND

1. Technical Field

What is disclosed herein relates to a detection device.

2. Description of the Related Art

Detection devices that include a light source and a sensor have been developed in recent years to detect a vascular pattern of, for example, veins located in a finger or a thumb, a wrist, or a leg. In a detection device of Japanese Translation of PCT International Application Publication Laid-open No. 2020-529695, the light source and the sensor are arranged so as to interpose an object to be detected therebetween. In such a detection device, light is emitted from the light source to the skin and enters the body. The light then passes through the blood, muscular tissues, and the like inside the body and further exits outside the body to be received by the sensor.

For example, when measuring biometric information such as pulsation or a blood oxygen saturation level ($SpO_2$) using an optical sensor, if the optical sensor receives external light components in addition to light from a light source for measurement, the detection device may detect a wavelength different from a desired wavelength. For this reason, detection devices that use optical sensors are desired to reduce the effect of the external light.

SUMMARY

According to an aspect, a detection device includes: a light source; a plurality of optical sensors that are arranged so as to be capable of receiving light of the light source and have light-receiving areas different in size; a detection circuit that is electrically coupled to each of the optical sensors and configured to detect waveform data that allows an amount of received light of each of the optical sensors to be identified; and a control circuit configured to select at least one piece of the waveform data having waveform amplitude that satisfies a selection condition from a plurality of pieces of the waveform data detected by the optical sensors.

DETAILED DESCRIPTION

Figure 1:
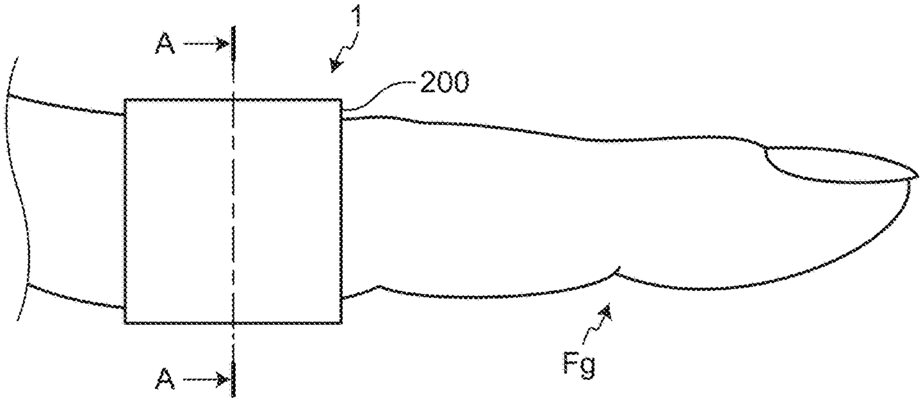
FIG. 1 is a schematic view illustrating an exemplary external view of a state where a finger is accommodated inside a detection device according to an embodiment, as viewed from a lateral side of a housing.

The following describes a mode (embodiment) for carrying out the disclosure in detail with reference to the drawings. The present disclosure is not limited to the description of the embodiment described below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the present specification and the drawings, and detailed description thereof may not be repeated where appropriate.

In the present specification and claims, in expressing an aspect of disposing another structure on or above a certain structure, a case of simply expressing “on” includes both a case of disposing the other structure immediately on the certain structure so as to contact the certain structure and a case of disposing the other structure above the certain structure with still another structure interposed therebetween, unless otherwise specified.

EMBODIMENT

Detection Device

Figure 2:
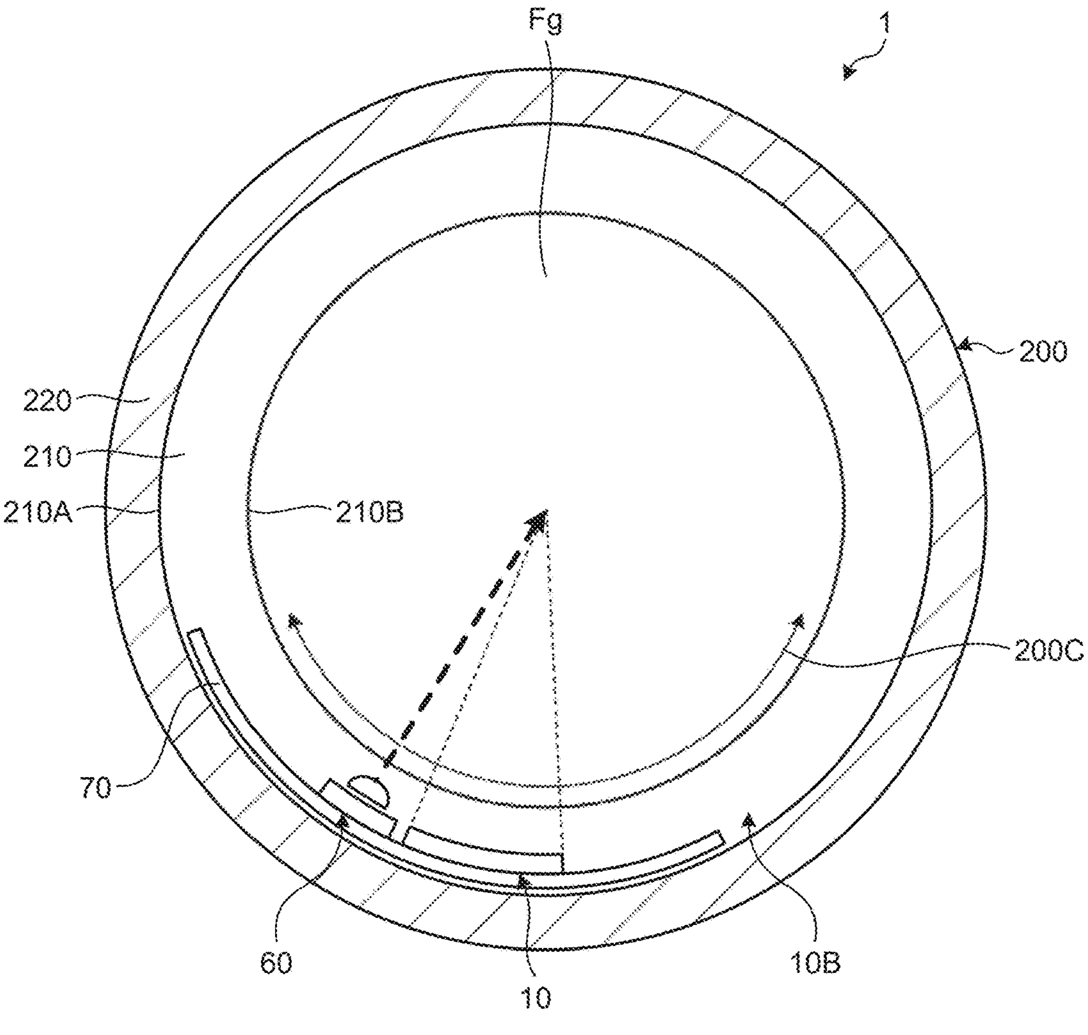
FIG. 2 is a schematic sectional view taken along section A-A illustrated in FIG. 1.
Figure 3:
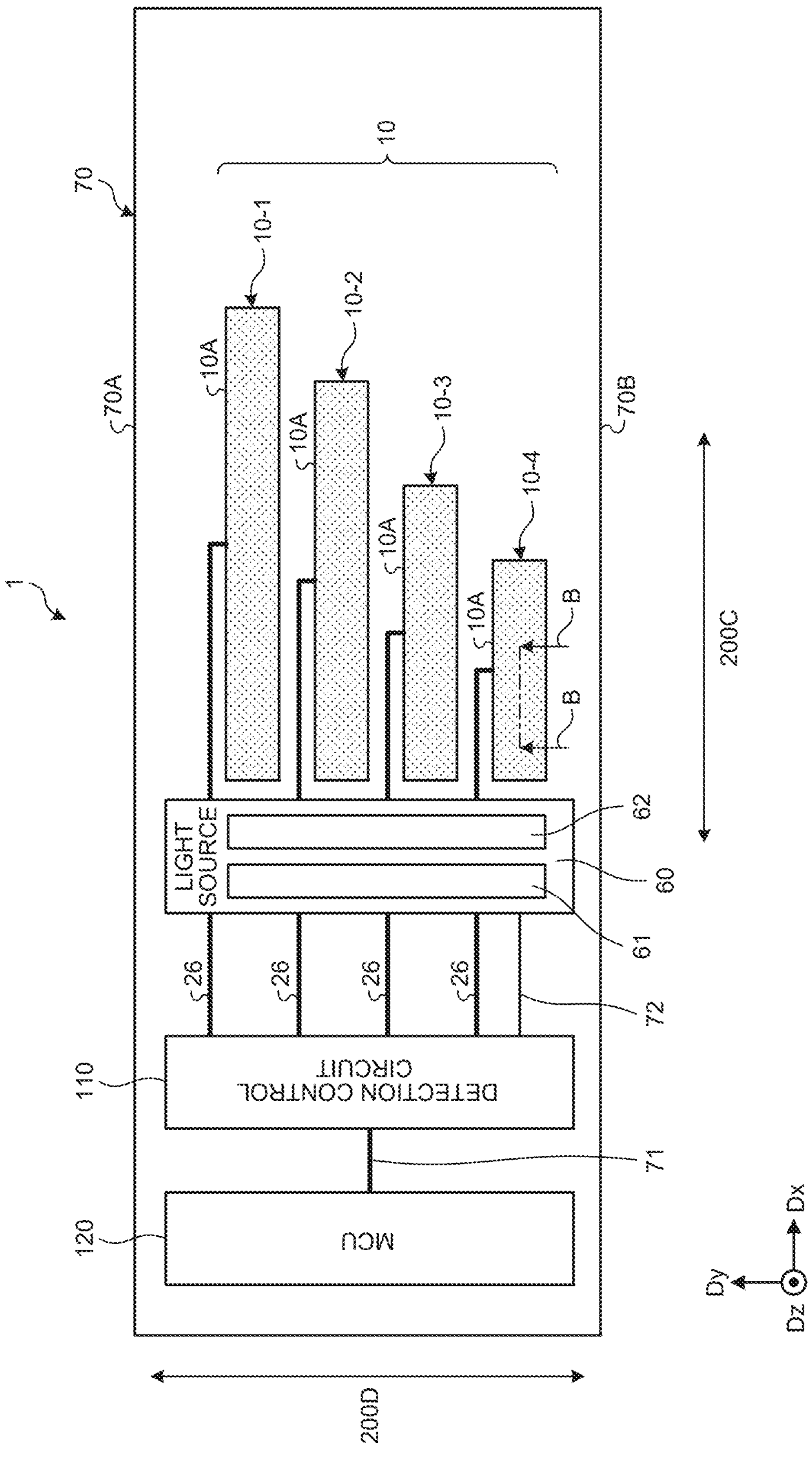
FIG. 3 is a schematic plan view illustrating an exemplary configuration of optical sensors and light sources of the detection device illustrated in FIG. 1.
Figure 4:
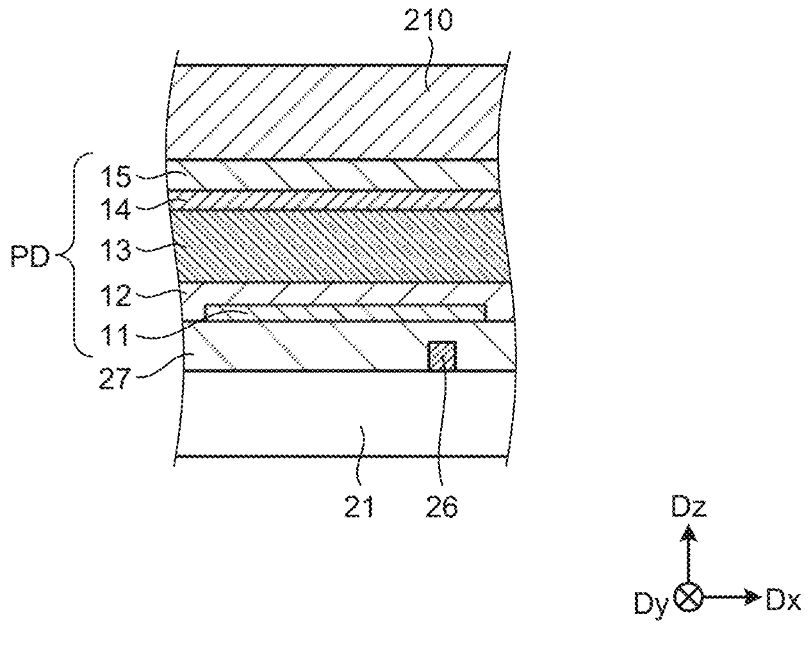
FIG. 4 is a schematic sectional view illustrating an exemplary multilayer configuration of one of the optical sensors taken along section B-B illustrated in FIG. 3.

FIG. 1 is a schematic view illustrating an exemplary external view of a state where a finger is accommodated inside a detection device according to an embodiment, as viewed from a lateral side of a housing. FIG. 2 is a schematic sectional view taken along section A-A illustrated in FIG. 1. FIG. 3 is a schematic plan view illustrating an exemplary configuration of optical sensors and light sources of the detection device illustrated in FIG. 1. FIG. 4 is a schematic sectional view illustrating an exemplary multilayer configuration of one of the optical sensors taken along section B-B illustrated in FIG. 3. FIG. 2 illustrates only the basic configuration of the detection device according to the embodiment and does not illustrate the other configurations.

A detection device 1 illustrated in FIG. 1 is a finger ring-shaped device that can be worn on and removed from a human body and is worn on a finger Fg of the human body. Examples of the finger Fg include a thumb, an index finger, a middle finger, a ring finger, and a little finger. The human body is a person to be authenticated whose identity is verified by the detection device 1. The detection device 1 can detect biometric information on a living body from the finger Fg wearing the detection device 1. The finger Fg is an example of a measurement target. The measurement target is the living body or a part of the living body, and is an object to be measured. The detection device 1 is made into a finger ring or a wristband so as to be easily carried by a user. In the following description, the detection device 1 is assumed to be used as the finger ring. The detection device 1 can use the detected biometric information for authentication of the person to be authenticated.

As illustrated in FIG. 2, the detection device 1 includes a housing 200, a light source 60, and a plurality of optical sensors 10. The detection device 1 is a device that includes a battery (not illustrated) in the housing 200 and is operated by power from the battery.

The housing 200 is formed in a ring shape (annular shape) that can be worn on the finger Fg, and is a wearable member to be worn on the living body. In the example illustrated in FIG. 2, the housing 200 includes a first housing 210 and a second housing 220. The first housing 210 is integrated with the second housing 220 to form the housing 200 into the ring shape. The first housing 210 is a member that makes contact with the human body wearing the housing 200. The first housing 210 accommodates therein the light source 60, the optical sensors 10, and so forth. The first housing 210 is formed into a ring shape using a housing material such as a light-transmitting synthetic resin or silicon. The second housing 220 has a surface of the housing 200 that covers an outer peripheral surface 210A of the first housing 210. The second housing 220 is formed into a ring shape using a member of, for example, a metal or a non-light-transmitting synthetic resin. The first housing 210 of the housing 200 accommodates therein a flexible printed circuit board 70 on which the light source 60, the optical sensors 10, and so forth are mounted. The flexible printed circuit board 70 is accommodated in the housing 200, for example, by forming the housing 200 by filling the periphery of the flexible printed circuit board 70 formed into a ring shape with a filling member in a mold.

As illustrated in FIG. 3, the flexible printed circuit board 70 is formed into a deformable band shape. The optical sensors 10, the light source 60, a detection control circuit 110 and a microcontroller unit (MCU) 120 are mounted on the flexible printed circuit board 70. The flexible printed circuit board 70 electrically couples the optical sensors 10 to the detection control circuit 110. The flexible printed circuit board 70 electrically couples the detection control circuit 110 to the MCU 120 via wiring 71. The flexible printed circuit board 70 electrically couples the detection control circuit 110 to the light source 60 via wiring 72.

In the following description, a first direction Dx is one direction in a plane parallel to the flexible printed circuit board 70 and is the same direction as a circumferential direction 200C. A second direction Dy is one direction in the plane parallel to the flexible printed circuit board 70 and is a direction orthogonal to the first direction Dx. The second direction Dy may non-orthogonally intersect the first direction Dx. A third direction Dz is a direction orthogonal to the first direction Dx and the second direction Dy. The third direction Dz is a direction normal to the flexible printed circuit board 70. The term “plan view” refers to a positional relation when viewed in a direction orthogonal to the flexible printed circuit board 70.

In the present embodiment, on the flexible printed circuit board 70, the optical sensors 10 having different lengths in the circumferential direction 200C along the first direction Dx are arranged in the second direction Dy that is a width direction 200D of the housing 200. The optical sensors 10 have different length in the circumferential direction 200C, and the longer the length in the circumferential direction 200C, the larger the area in plan view. On the flexible printed circuit board 70, an optical sensor 10-1 having the longest length and optical sensors 10-2, 10-3, and 10-4 having gradually decreasing lengths are arranged in this order in the second direction Dy from one end 70A toward another end 70B. On the flexible printed circuit board 70, the optical sensors 10 are arranged near the light source 60. This configuration allows the optical sensors 10 to detect light emitted by the light source 60 and reflected by the finger Fg (human body). The optical sensors 10 detect intensities of the light and converts them into electrical signals.

As illustrated in FIG. 2, the light source 60 is provided in the first housing 210 of the housing 200, and is configured to be capable of emitting the light toward the center of the housing 200. For example, an inorganic light-emitting diode (LED) or an organic electroluminescent (EL) diode (organic light-emitting diode (OLED)) is used as the light source 60. The light source 60 emits the light having a predetermined wavelength. The light source 60 includes a plurality of the LEDs so as to be capable of emitting infrared light, red light, and green light. The light source 60 is configured to be capable of selectively emitting the infrared light, the red light, and the green light.

In the example illustrated in FIG. 3, the light source 60 includes a first light source 61 and a second light source 62. The first light source 61 includes an LED that emits the infrared light, and the second light source 62 includes an LED that emits the red light. The first and the second light sources 61 and 62 are provided on the flexible printed circuit board 70 so as to have an equal distance from the optical sensors 10-1, 10-2, 10-3, and 10-4, thereby efficiently reducing the external light components. The first and the second light sources 61 and 62 may each be made up, for example, of one LED or a plurality of LEDS.

The light emitted from the light source 60 is reflected by a surface of an object to be detected, such as the finger Fg, and enters the optical sensor 10. Alternatively, the light emitted from the light source 60 may be reflected in the finger Fg or the like, or transmitted through the finger Fg or the like and enter a plurality of photodiodes PD of the optical sensor 10. Thereby, the detection device 1 can detect the information on the living body in the finger Fg or the like. Examples of the information on the living body include, but are not limited to, pulse waves and pulsation of the finger or a palm. That is, the detection device 1 may be configured as a vein detection device that detects the biometric information on veins or the like.

The optical sensors 10 are sensors that are provided to be arranged in the first housing 210 of the housing 200 and are capable of detecting light incident from an irradiation side of the light source 60. The irradiation side of the light source 60 is a side that irradiate the finger Fg serving as the measurement target wearing the housing 200. The irradiation side of the light source 60 accommodated inside the ring-shaped housing 200 is a side that emits light from the inside toward the outside of the housing 200, and is an inner peripheral surface 210B side of the housing 200 (refer to FIG. 2) to which the finger Fg serving as the measurement target comes close. The optical sensors 10 detect light that has been emitted by the light source 60 and reflected by the finger Fg or the like, light directly incident on the optical sensor, and other light. The optical sensors 10 are organic photodiodes (OPDs). As illustrated in FIG. 3, the optical sensors 10 are provided in the housing 200 while being arranged along the light source 60 in the width direction 200D (second direction Dy) of the housing 200.

In the embodiment, the optical sensors 10 include the optical sensors 10-1, 10-2, 10-3, and 10-4. In the following description, the optical sensors 10-1, 10-2, 10-3, and 10-4 will each be simply referred to as an optical sensor 10 when need not be distinguished from one another.

The optical sensors 10 have respective light-receiving areas 10A that are different in size. The size includes light-receiving sensitivity. Each of the light-receiving areas 10A is a planar area of the optical sensor 10 that receives light. The optical sensors 10 have the same length in the width direction 200D of the housing 200. In the embodiment, the light-receiving area 10A is formed in a rectangular shape extending along the circumferential direction 200C, but the shape is not limited to this shape, and may have a shape obtained by arranging a plurality of shapes.

By changing light-receiving areas of the optical sensors 10, the total amount of received light can be changed, although the ratio of amount of received light between the light from the light source 60 and the external light remains unchanged. The optical sensor 10-1 has the longest light-receiving area 10A in the circumferential direction 200C and has the largest light-receiving area. The optical sensor 10-2 has a shorter light-receiving area 10A than the optical sensor 10-1 in the circumferential direction 200C, and has a smaller light-receiving area than the optical sensor 10-1. The optical sensor 10-3 has a shorter light-receiving area 10A than the optical sensor 10-2 in the circumferential direction 200C, and has a smaller light-receiving area than the optical sensor 10-2. The optical sensor 10-4 has a shorter light-receiving area 10A than the optical sensor 10-3 in the circumferential direction 200C, and has a smaller light-receiving area than the optical sensor 10-3. The optical sensor 10-4 has approximately half the size of the optical sensor 10-1.

The optical sensor 10 includes an organic photodiode. As illustrated in FIG. 4, the optical sensor 10 includes a sensor substrate 21 and a corresponding one of the photodiodes PD. In the present embodiment, the optical sensor 10 further includes wiring lines 26 and an insulating layer 27. The insulating layer 27 is provided on the sensor substrate 21 so as to cover the wiring lines 26. The insulating layer 27 may be an inorganic insulating film or an organic insulating film. The wiring lines 26 may be formed in the same layer as a lower electrode 11.

The photodiode PD is provided on the insulating layer 27. The photodiode PD includes the lower electrode 11, a lower buffer layer 12, an active layer 13, an upper buffer layer 14, and an upper electrode 15. As the photodiode PD, the lower electrode 11, the lower buffer layer 12 (hole transport layer), the active layer 13, the upper buffer layer 14 (electron transport layer), and the upper electrode 15 are stacked in this order in the third direction Dz orthogonal to the sensor substrate 21.

The lower electrode 11 is an anode electrode of the photodiode PD, and is formed of a light-transmitting conductive material such as indium tin oxide (ITO), for example. The active layer 13 changes in characteristics (such as voltage-current characteristics and resistance value) according to light emitted thereto. An organic material is used as a material of the active layer 13. Specifically, the active layer 13 has a bulk heterostructure containing a mixture of a p-type organic semiconductor and an n-type fullerene derivative ((6,6)-phenyl-$C_{61}$-butyric acid methyl ester (PCBM)) that is an n-type organic semiconductor. As the active layer 13, low-molecular-weight organic materials can be used including, for example, fullerene ($C_{60}$), phenyl-$C_{61}$-butyric acid methyl ester (PCBM), copper phthalocyanine (CuPc), fluorinated copper phthalocyanine ($F_{16}CuPc$), 5,6,11,12-tetraphenyltetracene (rubrene), and perylene diimide (PDI) (derivative of perylene).

The active layer 13 can be formed by a vapor deposition process (dry process) using any of the low-molecular-weight organic materials listed above. In this case, the active layer 13 may be, for example, a multilayered film of CuPc and $F_{16}CuPc$, or a multilayered film of rubrene and $C_{60}$. The active layer 13 can also be formed by a coating process (wet process). In this case, the active layer 13 is made using a material obtained by combining any of the above-listed low-molecular-weight organic materials with a high-molecular-weight organic material. As the high-molecular-weight organic material, for example, poly(3-hexylthiophene) (P3HT) and F8-alt-benzothiadiazole (F8BT) can be used. The active layer 13 can be a film made of a mixture of P3HT and PCBM, or a film made of a mixture of F8BT and PDI.

The lower buffer layer 12 is a hole transport layer. The upper buffer layer 14 is an electron transport layer. The lower buffer layer 12 and the upper buffer layer 14 are provided to facilitate holes and electrons generated in the active layer 13 to reach the lower electrodes 11 or the upper electrode 15. The lower buffer layer 12 (hole transport layer) is in direct contact with the top of the lower electrode 11 and is also provided in an area between the adjacent lower electrodes 11. The active layer 13 is in direct contact with the top of the lower buffer layer 12. The material of the hole transport layer is a metal oxide layer. For example, tungsten oxide ($WO_3$) or molybdenum oxide is used as the metal oxide layer.

The upper buffer layer 14 (electron transport layer) is in direct contact with the top of the active layer 13, and the upper electrode 15 is in direct contact with the top of the upper buffer layer 14. Polyethylenimine ethoxylated (PEIE) is used as a material of the electron transport layer.

The materials and the manufacturing methods of the lower buffer layer 12, the active layer 13, and the upper buffer layer 14 are merely exemplary, and other materials and manufacturing methods may be used. For example, each of the lower buffer layer 12 and the upper buffer layer 14 is not limited to a single-layer film, and may be formed as a multilayered film that includes an electron blocking layer and a hole blocking layer.

The upper electrode 15 is provided on the upper buffer layer 14. The upper electrode 15 is a cathode electrode of the photodiode PD, and is continuously formed over the whole optical sensors 10. In other words, the upper electrode 15 is continuously provided on the photodiodes PD. The upper electrode 15 faces the lower electrodes 11 with the lower buffer layer 12, the active layer 13, and the upper buffer layer 14 interposed therebetween. The upper electrode 15 is formed, for example, of a light-transmitting conductive material such as ITO or indium zinc oxide (IZO). The upper electrode 15 is electrically coupled to a power supply circuit, which is not illustrated. The photodiodes PD are well sealed by providing the first housing 210 on the upper electrode 15 and so forth.

Each of the optical sensors 10 is electrically coupled to the detection control circuit 110 via the wiring line 26 provided on the flexible printed circuit board 70. In other words, the detection control circuit 110 is electrically coupled to the lower electrodes 11 of the optical sensors 10 via the wiring lines 26. Each of the photodiodes PD of the optical sensors 10 outputs an electrical signal corresponding to light emitted thereto as a detection signal Vdet to the detection control circuit 110. As a result, each of the optical sensors 10 outputs the electrical signal corresponding to the light emitted to the light-receiving area 10A as the detection signal Vdet to the detection control circuit 110.

The detection control circuit 110 controls the detection operation by supplying control signals to the photodiodes PD of the optical sensors 10, and detects information on the object to be detected based on the detection signal Vdet from the photodiode PD for each of the optical sensors 10. The detection control circuit 110 includes an analog front-end (AFE) circuit, for example. The detection control circuit 110 is a signal processing circuit having functions of at least a detection signal amplifier and an analog-to-digital (A/D) converter. The detection signal amplifier amplifies the detection signals Vdet. The A/D converter converts analog signals output from the detection signal amplifier into digital signals.

The MCU 120 is electrically coupled to the detection control circuit 110. The MCU 120 executes processing based on the detection results of the detection control circuit 110. The MCU 120 can perform, for example, a process to calculate a blood oxygen saturation level ($SpO_2$) from a ratio in hemoglobin absorbance at wavelengths detected by the detection control circuit 110. The blood oxygen saturation level ($SpO_2$) refers to a ratio of an amount of oxygen actually bound to hemoglobin to the total amount of oxygen under the assumption that the oxygen is bound to all the hemoglobin in the blood. The MCU 120 can display the biometric information, including the blood oxygen saturation level and other information, on a display device or transmit the information via a communication device. The MCU 120 has a function to compare the information on the living body detected by the detection control circuit 110 with authentication information stored in advance and authenticate the person to be authenticated based on the result of the comparison. The MCU 120 has a function to control transmission of the information on the living body to an external device via a communication device, which is not illustrated.

The configuration example of the detection device 1 according to the present embodiment has been described above. The configuration described above using FIGS. 1 to 4 is merely an example, and the configuration of the detection device 1 according to the present embodiment is not limited to the example. The configuration of the detection device 1 according to the present embodiment can be flexibly modified according to specifications and/or operations.

Figure 5:
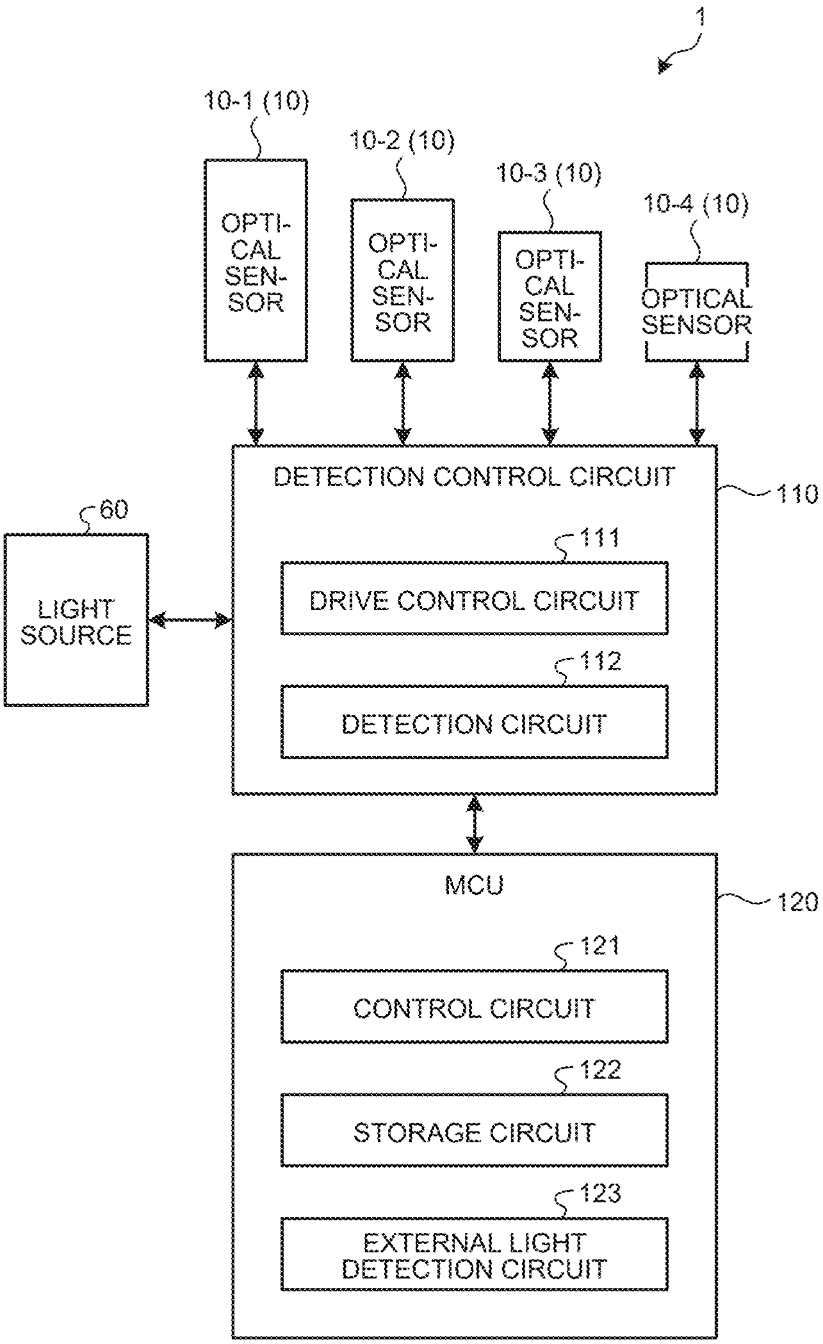
FIG. 5 is a block diagram illustrating an exemplary configuration of the detection device according to the embodiment.
Figure 6:
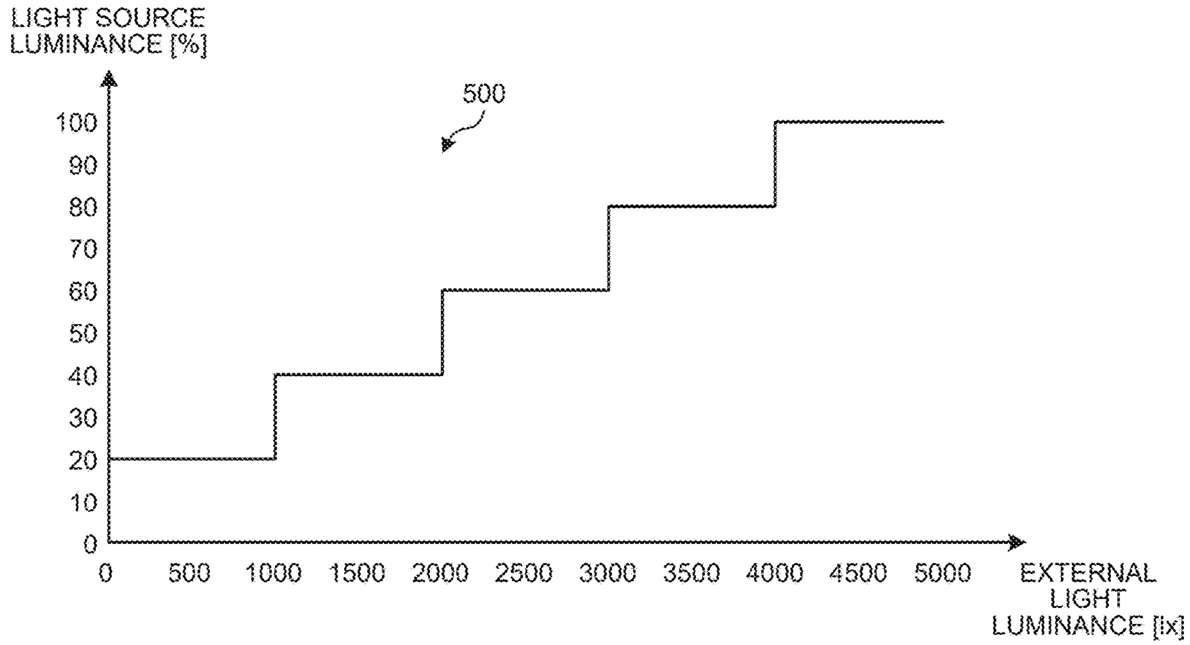
FIG. 6 is a diagram illustrating exemplary table data for obtaining light source luminance from luminance of external light.

FIG. 5 is a block diagram illustrating an exemplary configuration of the detection device 1 according to the embodiment. FIG. 6 is a diagram illustrating exemplary table data for obtaining light source luminance from luminance of the external light.

As illustrated in FIG. 5, the detection device 1 includes the four optical sensors 10-1, 10-2, 10-3, and 10-4, the detection control circuit 110, and the MCU 120. The detection control circuit 110 is an example of a detection circuit.

The optical sensor 10 is an optical sensor including the photodiode PD that is a photoelectric conversion element. The photodiode PD included in the optical sensor 10 outputs the electrical signal corresponding to the light emitted thereto as the detection signal Vdet to the detection control circuit 110. The optical sensor 10 detects the light in response to a gate drive signal supplied from the detection control circuit 110.

The detection control circuit 110 includes a drive control circuit 111 and a detection circuit 112.

The drive control circuit 111 is a circuit that supplies control signals to the respective optical sensors 10 to control operations thereof. The drive control circuit 111 supplies various control signals such as a start signal STV, a clock signal CK, and a reset signal RST1 to the optical sensors 10. The drive control circuit 111 supplies, in accordance with instructions from the MCU 120, various control signals to the light source 60 to control lighting and non-lighting thereof.

The detection circuit 112 is an analog front-end (AFE) circuit, for example. The detection circuit 112 detects an analog signal from each of the optical sensors 10. Using a switch circuit that sequentially or simultaneously selects a plurality of signal lines, the detection circuit 112 can select the signal lines to be used for detection. The detection circuit 112 can output the detected analog signal to the MCU 120 as a detection signal of the optical sensor 10. The detection circuit 112 can output the detection signal from each of the four optical sensors 10-1, 10-2, 10-3, and 10-4 to the MCU 120.

The MCU 120 includes a control circuit 121, a storage circuit 122, and an external light detection circuit 123.

The control circuit 121 has a function to acquire the detection signals simultaneously detected by the optical sensors 10 and convert the detection signals from the analog signals to digital signals. The control circuit 121 stores waveform data indicated by the acquired detection signals in the storage circuit 122 so as to be associated with the optical sensors 10. The control circuit 121 selects waveform data having amplitude of waveforms satisfying selection conditions, from a plurality of pieces of the waveform data acquired from the optical sensors 10. The control circuit 121 selects, from a plurality of pieces of the waveform data, the waveform data having the largest average value of a plurality of amplitude values of the waveforms indicated by the waveform data. Examples of the amplitude include the peak-to-peak distance of a waveform, the distance from the center of the waveform to the maximum displacement, and so forth. In the present embodiment, the control circuit 121 calculates the average value of a predetermined number of peak-to-peak amplitude values in the waveforms indicated by the waveform data, and selects the waveform data having the largest average value from a plurality of pieces of the waveform data. The predetermined number is set, for example, so as to uniform the number of amplitude values to be compared in a plurality of pieces of the waveform data.

If the average values of amplitude values of a plurality of pieces of the waveform data are the same, the control circuit 121 selects the waveform data according to a predetermined priority order. The average values of amplitude values being the same means that the average values are equal to each other or that the average values differ from one another within an error range. Examples of the predetermined priority order include, but are not limited to, a priority order assigned to the four optical sensors 10-1, 10-2, 10-3, and 10-4. In the present embodiment, the predetermined priority order is set such that the priority gradually decreases in the order of the optical sensors 10-1, 10-2, 10-3, and 10-4. When the average values of amplitude values of a plurality of pieces of the waveform data are the same, the control circuit 121 selects the waveform data of the optical sensor 10 having a smaller area of the light-receiving area 10A. An example of the selection by the control circuit 121 will be described later.

The storage circuit 122 temporarily stores therein signals calculated by the control circuit 121. The storage circuit 122 may be, for example, a random-access memory (RAM) or a register circuit. The storage circuit 122 can store therein information such as the selection conditions used by the control circuit 121.

The external light detection circuit 123 has a function to detect the external light intensity of the detection device 1. The external light detection circuit 123 detects the external light intensity based on the detection signals simultaneously detected by the optical sensors 10. The external light detection circuit 123 detects the external light intensity based on the waveform data from any one of the optical sensors 10. The external light detection circuit 123 uses the waveform data of the optical sensor 10 having the largest size of the light-receiving area 10A among the optical sensors 10. The external light detection circuit 123 supplies external light intensity information including the value of the detected external light intensity to the control circuit 121.

After being supplied with the external light intensity information from the external light detection circuit 123, the control circuit 121 sets the luminance of the light source 60 to a value corresponding to the external light intensity of the external light intensity information. As illustrated in FIG. 6, the detection device 1 stores, in the storage circuit 122, table data 500 for obtaining the light source luminance from the luminance of the external light. In the example illustrated in FIG. 6, the horizontal axis indicates the external light luminance (lx), and the vertical axis indicates the light source luminance (%). The table data 500 is a table that associates the external light luminance with the light source luminance in a stepwise manner and is used to obtain the light source luminance from the external light luminance. For example, the control circuit 121 sets the luminance of the light source 60 to 20% if the external light intensity received from the external light detection circuit 123 is lower than 1000 lx, and sets the luminance of the light source 60 to 100% if the external light intensity received from the external light detection circuit 123 is equal to or higher than 4000 lx. For example, the control circuit 121 sets the luminance of the light source 60 in a stepwise manner if the external light intensity received from the external light detection circuit 123 is equal to or higher than 1000 lx and lower than 4000 lx. The external light detection circuit 123 may be included in the control circuit 121.

Figure 7:
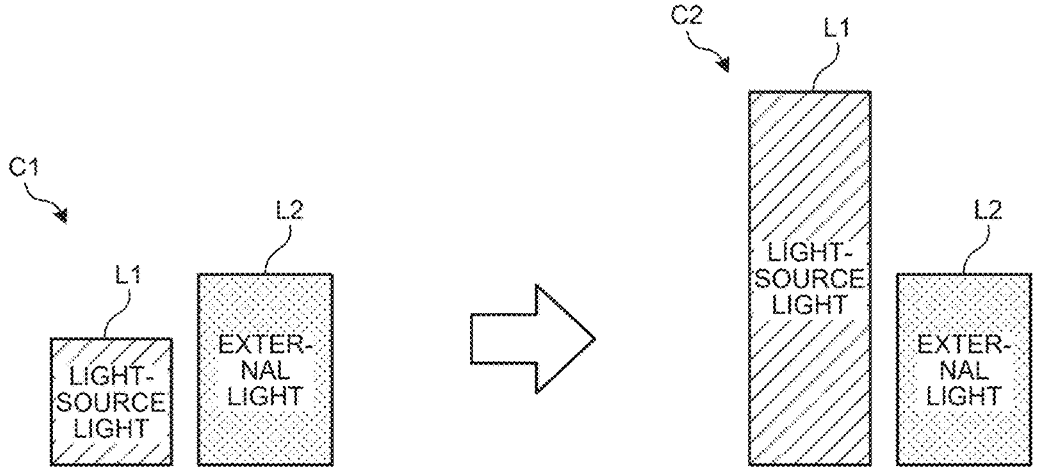
FIG. 7 is a diagram for explaining exemplary sensor light receiving ratios of an optical sensor for reference.

The following describes the external light components in the detection device 1. FIG. 7 is a diagram for explaining exemplary sensor light receiving ratios of an optical sensor for reference.

In Scene C1 illustrated in FIG. 7, in the detection device 1, if the amount of light-source light L1 received from the light source 60 is smaller than the amount of external light L2 received from outside, the detection circuit 112 detects components having different wavelengths from a desired wavelength. That is, in the detection device 1, a valid signal value is obscured in the external light components. To ignore this effect, the light source 60 having higher luminance is required as the level of the external light increases. However, as illustrated in Scene C2, in the detection device 1, if the luminance of the light source 60 is increased, the amount of the light-source light L1 received from the light source 60 becomes larger than the amount of the external light L2 received from outside, but falls out of the dynamic range of the A/D converter. That is, in the detection device 1, increasing the luminance of the light source 60 also increases the total amount of the received light, so that the amount of the light-source light L1 received from the light source 60 is limited by the dynamic range.

The dynamic range may be adjusted by changing the exposure time according to the level of the light entering the optical sensor 10, but the optical sensor 10 is week in detection while the external light L2 changes over time. That is, the optical sensor 10 cannot follow sudden changes, thus generating periods during which data cannot be detected.

In order to detect the desired wavelength using the MCU 120 even when the external light components are present, the detection device 1 according to the present embodiment uses the optical sensors 10-1, 10-2, 10-3, and 10-4 having different light-receiving areas.

Figure 8:
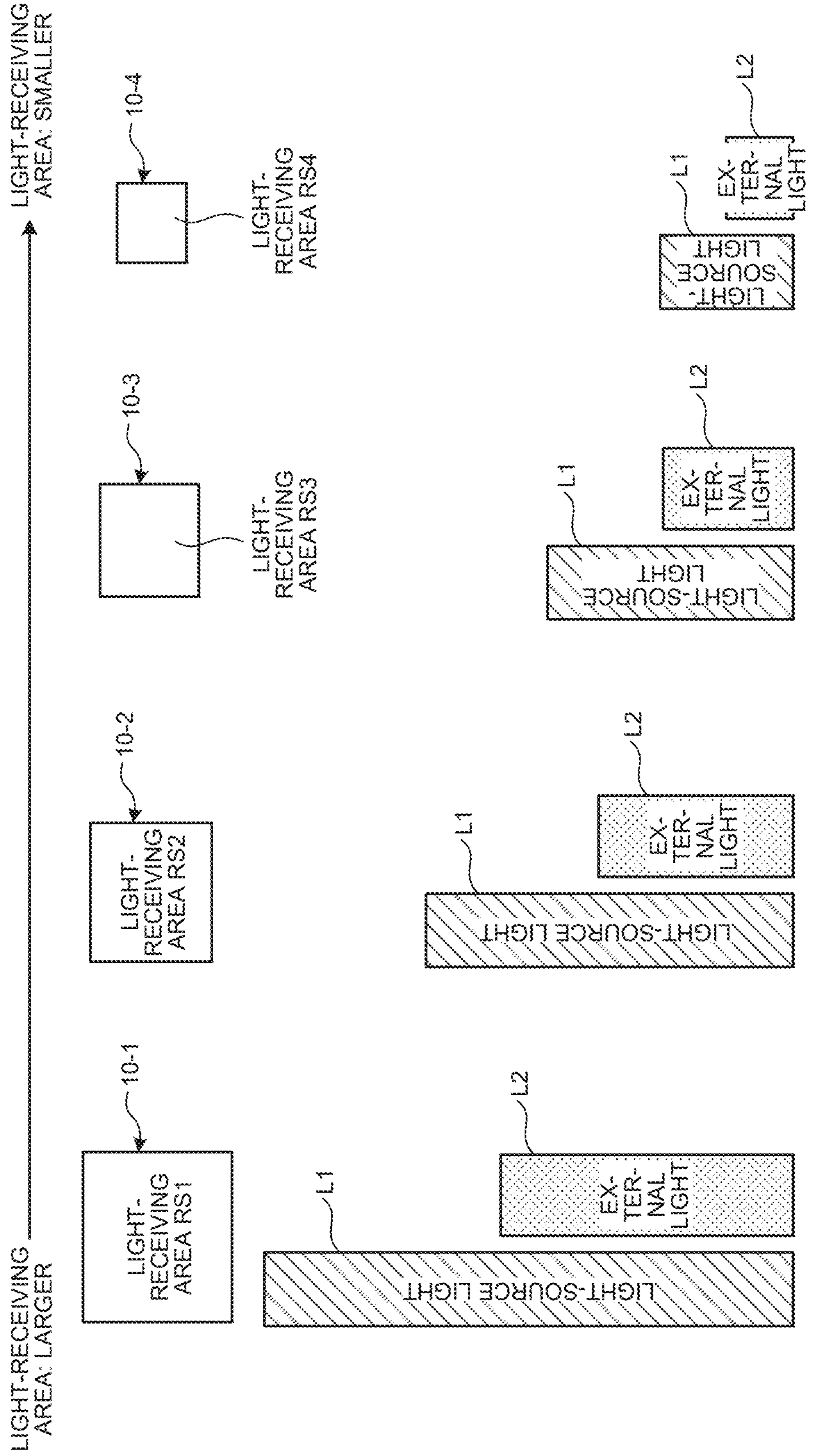
FIG. 8 is a diagram for explaining an exemplary relation between a light-receiving area of an optical sensor, light-source light, and the external light.

FIG. 8 is a diagram for explaining an exemplary relation between the light-receiving area of the optical sensor 10, the light-source light L1, and the external light L2. As illustrated in FIG. 8, the detection device 1 includes the optical sensors 10-1, 10-2, 10-3, and 10-4 having different sizes (sensitivity) of the light-receiving area 10A and selects the waveform data of the optical sensor 10 having amplitude of the acquired waveform data satisfying the selection condition. The selection conditions include, for example, a condition for selecting the waveform data having the largest amplitude. The selection conditions include, for example, a condition for selecting the waveform data having the largest peak-to-peak amplitude. The selection conditions include, for example, a condition for selecting the waveform data having amplitude equal to or larger than a threshold or having amplitude that is the average value of amplitude values equal to or larger than the threshold.

In the example illustrated in FIG. 8, the area of the light-receiving area 10A decreases in the order of a light-receiving area RS1 of the optical sensor 10-1, a light-receiving area RS2 of the optical sensor 10-2, a light-receiving area RS3 of the optical sensor 10-3, and a light-receiving area RS4 of the optical sensor 10-4. In the detection device 1, the amount of the light-source light L1 received by the optical sensor 10-1 is the largest, and the amount of the light-source light L1 received from the light source 60 decreases in the order of the optical sensors 10-2, 10-3, and 10-4. In the detection device 1, the ratio of the amount of received light between the light-source light L1 and the external light L2 is 2:1 in all the optical sensors 10.

Thus, the detection device 1 can reduce the total amount of received light when the light-receiving areas RS1, RS2, RS3, and RS4 are different from one another, while the ratio of the light-source light L1 to the external light L2 remains the same. The detection device 1 can restrain the wavelength components of the external light L2 from being mixed in with the desired wavelength by selecting the optical sensor 10 that is optimal.

Exemplary Selection Method of Detection Device

Figure 9:
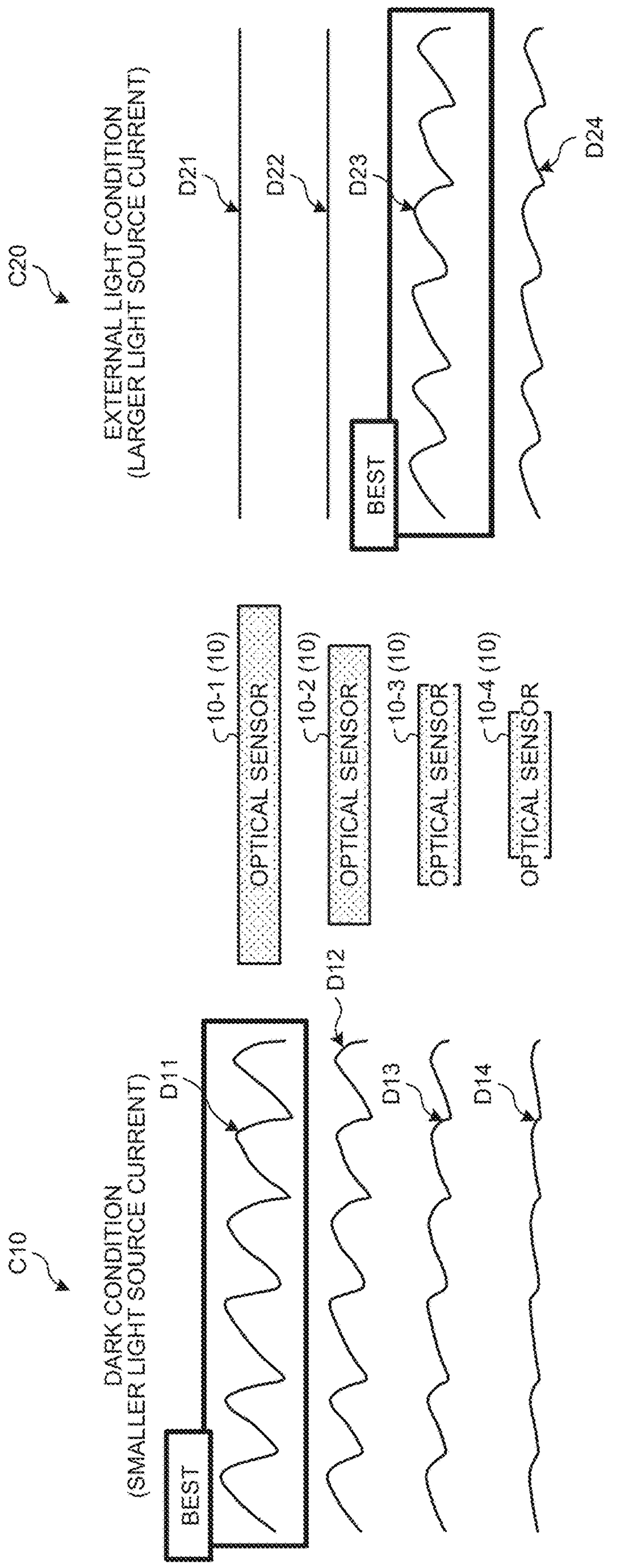
FIG. 9 is a diagram illustrating an exemplary selection method of the detection device according to the embodiment.

FIG. 9 is a diagram illustrating an exemplary selection method of the detection device 1 according to the embodiment. Scene C10 of FIG. 9 illustrates the waveform data detected by the optical sensors 10 of the detection device 1 when the light source 60 is turned on with a small current under a dark condition. The dark condition refers to a condition where the detection device 1 is less affected by the external light. The optical sensor 10-1 outputs waveform data D11 corresponding to the light-source light L1 received from the light source 60. The optical sensor 10-2 outputs waveform data D12 corresponding to the light-source light L1 received from the light source 60. The optical sensor 10-3 outputs waveform data D13 corresponding to the light-source light L1 received from the light source 60. The optical sensor 10-4 outputs waveform data D14 corresponding to the light-source light L1 received from the light source 60.

Under the dark condition, the detection device 1 reduces power consumption by selecting the optical sensor 10 having as high sensitivity as possible and minimizing the current for driving the light source 60. For example, the detection device 1 respectively calculates the average values of the amplitude values of the waveforms indicated by the waveform data D11, D12, D13, and D14 in the same period of time, and selects the waveform data having the largest average value. Alternatively, the detection device 1 selects the waveform data having the largest waveform amplitude among the waveforms indicated by the waveform data D11, D12, D13, and D14 in the same detection period of time. In the dark condition illustrated in Scene C10 of FIG. 9, the detection device 1 selects the waveform data D11 having the largest peak-to-peak amplitude from the waveform data D11, D12, D13, and D14, as the best (optimal) waveform data of the optical sensor 10.

In order to calculate the blood oxygen saturation level ($SpO_2$) under an external light condition, the detection device 1 needs to increase the current of the light source 60 according to the external light intensity. The external light condition refers to a condition under which the detection device 1 is affected by the external light. If the sensitivity of the optical sensor 10 is high under the external light condition, the waveform of the optical sensor 10 is saturated. Therefore, the detection device 1 selects the optical sensor 10 having lower sensitivity.

Scene C20 of FIG. 9 illustrates the waveform data detected by the optical sensors 10 of the detection device 1 when the light source 60 is turned on with a large current under the external light condition. The optical sensor 10-1 outputs waveform data D21 including the external light L2. The optical sensor 10-2 outputs waveform data D22 including the external light L2. The optical sensor 10-3 outputs waveform data D23 including the external light L2. The optical sensor 10-4 outputs the waveform data D24 including the external light L2.

Under the external light condition illustrated in Scene C20 of FIG. 9, the detection device 1 selects the waveform data D23 having a larger waveform amplitude value as the best (optimal) waveform data of the optical sensor 10 under the external light condition from among the waveform data D23 and the waveform data D24, instead of the waveform data D21 and the waveform data D22, the waveforms of which are saturated. That is, the detection device 1 selects the optical sensor 10 having lower sensitivity under the external light condition. Thus, the detection device 1 continues to take the waveform data of all the optical sensors 10 and selects the waveform data suitable for the selection condition from among pieces of the waveform data. Therefore, the waveform data is avoided from being damaged even if the external light suddenly changes.

Example of Processing Procedure of Detection Device According to Embodiment

Figure 10:
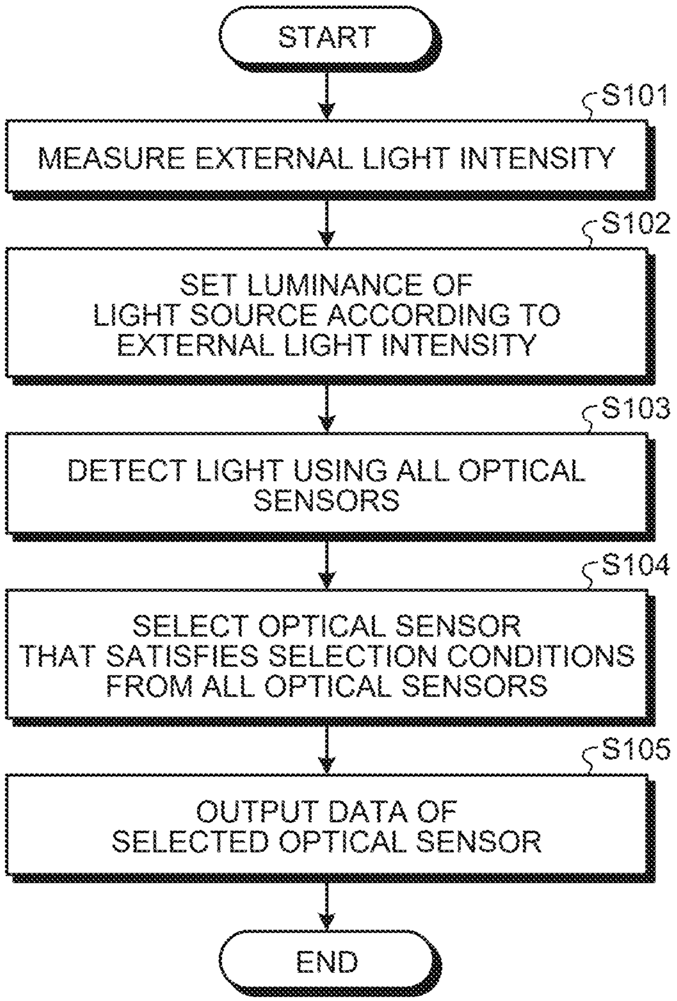
FIG. 10 is a flowchart illustrating an exemplary processing procedure executed by the detection device according to the embodiment.

The following describes a processing procedure of the detection device 1 worn on the finger Fg. FIG. 10 is a flowchart illustrating an exemplary processing procedure executed by the detection device 1 according to the embodiment. The detection device 1 repeatedly executes the processing procedure illustrated in FIG. 10, for example, at the detection timing when the detection device 1 is worn on the finger Fg. Examples of the detection timing include, but are not limited to, the time of authentication, preset date and time or a time zone, and when the device is worn on the finger Fg.

As illustrated in FIG. 10, the detection device 1 measures the external light intensity (Step S101). For example, the detection device 1 drives any one or at least one of the optical sensors 10-1, 10-2, 10-3, and 10-4, acquires the waveform data detected by the driven optical sensor 10, and measures the external light intensity based on the waveform data. In this case, the detection device 1 does not turn on the light source 60. Therefore, the amount of light (light intensity) detected by the optical sensor 10 is the amount of the external light L2. After the detection device 1 stores the measured external light intensity of the external light L2 in the storage circuit 122, the process proceeds to Step S102.

The detection device 1 sets the luminance of the light source 60 according to the external light intensity (Step S102). For example, the detection device 1 identifies the light source luminance corresponding to the external light intensity using the external light intensity measured at Step S101 and the table data 500 (refer to FIG. 6) described above, and sets the identified light source luminance as the luminance of the light source 60. After the process at Step S102 ends, the detection device 1 performs a process at Step S103.

The detection device 1 detects light using all the optical sensors 10 (Step S103). For example, the detection device 1 turns on the first light source 61 or the second light source 62 of the light source 60 at the set luminance, acquires the waveform data detected by the detection circuit 112 for each of the optical sensors 10-1, 10-2, 10-3, and 10-4, and stores the acquired waveform data in the storage circuit 122. After the process at Step S103 ends, the detection device 1 performs a process at Step S104. The detection device 1 may turn on the light source 60 at Step S102.

The detection device 1 selects the optical sensor 10 that satisfies the selection condition from all the optical sensors 10 (Step S104). For example, the detection device 1 identifies the waveform data having the waveform amplitude satisfying the selection condition from a plurality of pieces of the waveform data of the optical sensors 10-1, 10-2, 10-3, and 10-4. For example, the detection device 1 identifies the waveform data having the largest waveform amplitude, the waveform data having the largest peak-to-peak distance, or the like from a plurality of pieces of the waveform data for each of the optical sensors 10. Alternatively, the detection device 1 calculates the average value of a predetermined number of the amplitudes of the waveform indicated by the waveform data, for each piece of the waveform data of the optical sensors 10-1, 10-2, 10-3, and 10-4; and identifies the waveform data having the largest average value. The detection device 1 then selects the optical sensor 10 that has detected the identified waveform data as the optical sensor 10 that satisfies the selection condition. After the process at Step S104 ends, the detection device 1 performs a process at Step S105.

The detection device 1 outputs the data of the selected optical sensor 10 (Step S105). For example, the detection device 1 requests a display apparatus, a smartphone, or the like to output the waveform data selected at Step S104. Thus, the detection device 1 can output the waveform data less affected by the external light. After the process at Step S105 ends, the detection device 1 ends the processing procedure illustrated in FIG. 10.

The detection device 1 executes the predetermined procedure illustrated in FIG. 10 so as to turn on the first light source 61 and acquire and output the waveform data, and then, executes the predetermined procedure illustrated in FIG. 10 so as to turn on the second light source 62 and acquire and output the waveform data. In this way, the detection device 1 alternately turns on the first and the second light sources 61 and 62, and acquires the signals having wavelength components of the respective light sources in a time-division manner. The detection device 1 then performs the process to calculate the blood oxygen saturation level ($SpO_2$) based on the ratio in hemoglobin absorbance at two wavelengths (red light/infrared light). The detection device 1 displays the biometric information, including the blood oxygen saturation level and other information, on the display device or transmit the information via the communication device.

The detection device 1 can select the waveform data having the waveform amplitude satisfying the selection condition from a plurality of pieces of the waveform data of the optical sensors 10-1, 10-2, 10-3, and 10-4. Therefore, the detection device 1 can reduce the effect of the external light when making measurements using the optical sensor 10 even under environments affected by the external light. As a result, the detection device 1 can improve accuracy of detection without requiring components such as a cover to block the external light.

The detection device 1 can detect the external light intensity, and increase the amount of light to be emitted as the external light intensity is higher. Thus, the detection device 1 can increase the amount of light from the light source 60 as the level of the external light increases, therefore restraining the valid waveform data from being buried in the external light components.

The detection device 1 can reduce effects of changes under measurement environments by selecting the waveform data having the largest average value of the predetermined number of amplitudes of the waveform indicated by the waveform data. If the average values of the amplitudes indicated by a plurality of pieces of the waveform data are the same, the detection device 1 selects the waveform data according to the predetermined priority order, thus achieving detection using the waveform data of the appropriate optical sensor 10. If the average values of the amplitudes indicated by a plurality of pieces of the waveform data are the same, the detection device 1 selects the waveform data of the optical sensor 10 having a smaller area of the light-receiving area 10A, thus selecting the waveform data of the appropriate optical sensor 10 under the external light condition.

The detection device 1 can appropriately detect the effect of the external light in a measurement environment by detecting the external light intensity based on the waveform data of any one of the optical sensors 10. Using the waveform data of the optical sensor 10 having the largest light-receiving area 10A among the optical sensors 10, the detection device 1 can even more appropriately detect the effect of the external light in the measurement environment.

Modifications of Embodiment

In the embodiment, the configuration of the detection device 1 in which the four optical sensors 10-1, 10-2, 10-3, and 10-4 are arranged along the width direction 200D of the housing 200 has been described, but the embodiment is not limited to this configuration.

Figure 11:
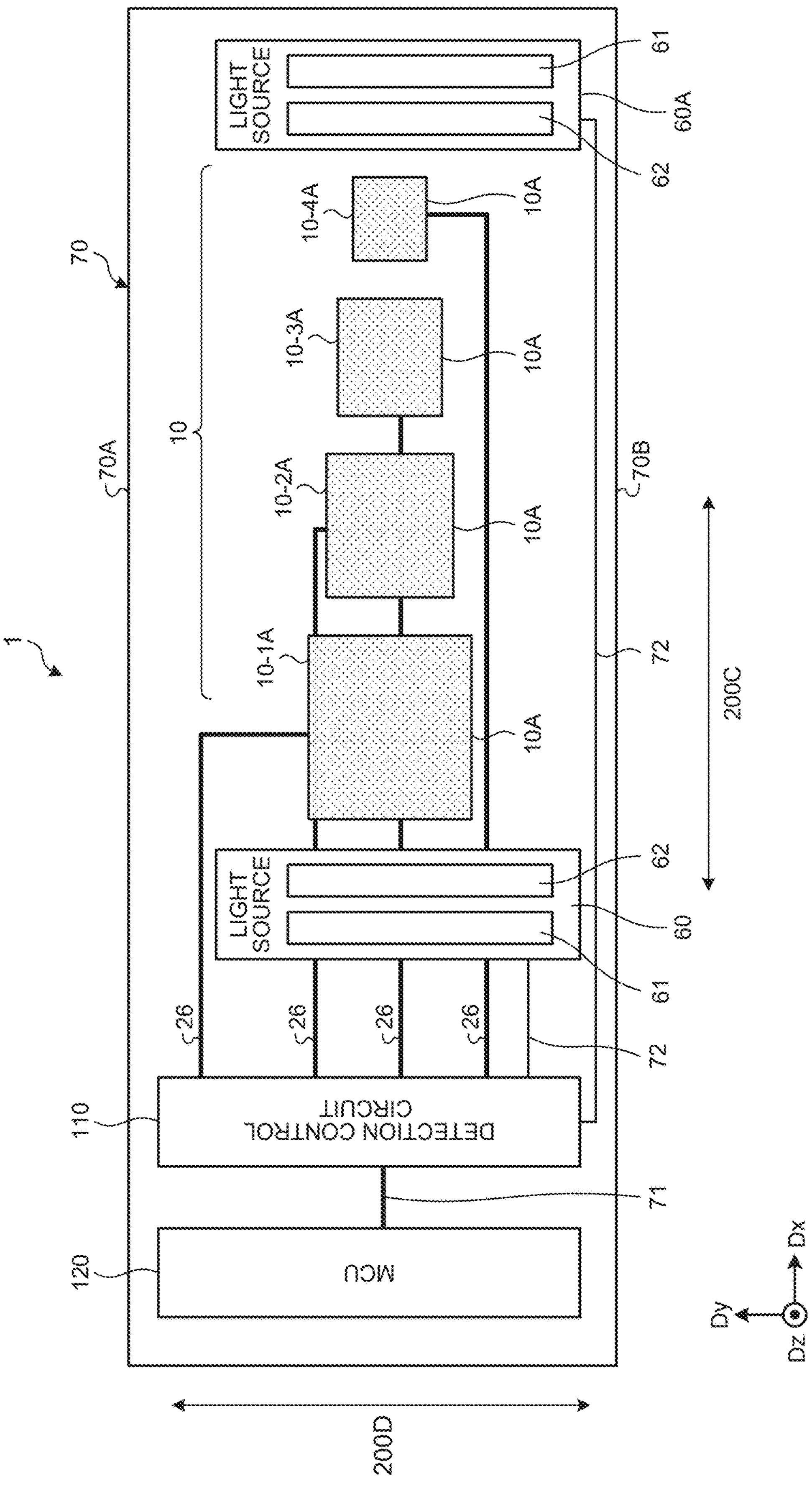
FIG. 11 is a schematic plan view illustrating an exemplary configuration of the optical sensors and the light sources of the detection device according to a modification of the embodiment.

FIG. 11 is a schematic plan view illustrating an exemplary configuration of the optical sensors 10 and the light source 60 of the detection device 1 according to a modification of the embodiment. As illustrated in FIG. 11, in the detection device 1, a plurality of optical sensors 10, a plurality of light sources 60, the detection control circuit 110, and the MCU 120 are mounted on the flexible printed circuit board 70. The optical sensor 10 includes an optical sensor 10-1A, an optical sensor 10-2A, an optical sensor 10-3A, and an optical sensor 10-4A. The detection device 1 may have a configuration in which the optical sensors 10-1A, 10-2A, 10-3A, and 10-4A are arranged along the circumferential direction 200C of the housing 200. The optical sensors 10-1A, 10-2A, 10-3A, and 10-4A are the same as the optical sensors 10-1, 10-2, 10-3, and 10-4 described above in area of the light-receiving area 10A, but differ from the optical sensors 10-1, 10-2, 10-3, and 10-4 in shape of the light-receiving area 10A. The optical sensors 10-1A, 10-2A, 10-3A, and 10-4A have different sizes (lengths) in the circumferential direction 200C and the width direction 200D.

The detection device 1 provides the light sources 60 near the optical sensors 10-1A and 10-4A in the circumferential direction 200C of the housing 200. That is, the detection device 1 includes two light sources 60 and 60A, and the two light sources 60 and 60A are electrically coupled to the detection control circuit 110 via the wiring 72. Each of the two light sources 60 and 60A includes the first light source 61 and the second light source 62. The optical sensor 10-1A is closer to the second light source 62 than the first light source 61. The optical sensor 10-4A is closer to the second light source 62 than the first light source 61.

Thus, the detection device 1 can expand the detection area of the optical sensors 10 by arranging the four optical sensors 10 along the circumferential direction 200C of the housing 200. This configuration allows the detection device 1 to acquire the waveform data less affected by the external light even when the detection area of the optical sensors 10 is expanded.

The example illustrated in FIG. 11 describes the case where the detection device 1 is provided with the two light source 60 on both sides of optical sensors 10 in the circumferential direction 200C of the housing 200, but the configuration is not limited to this case. For example, the detection device 1 may have a configuration in which one light source 60 is located adjacent to one of the optical sensors 10-1A and 10-4A when the optical sensors 10 are arranged along the circumferential direction 200C of the housing 200. Alternatively, for example, the detection device 1 may have a configuration in which the light sources 60 are arranged along the optical sensors 10 between the one end 70A or the other end 70B of the flexible printed circuit board 70 and the optical sensors 10.

Figure 12:
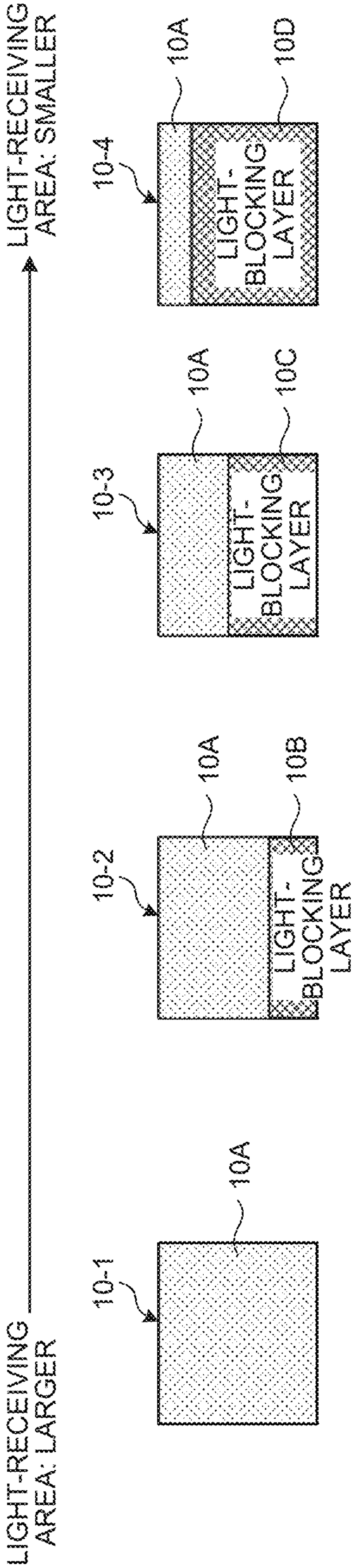
FIG. 12 is a diagram illustrating another exemplary configuration of the optical sensors illustrated in FIG. 11.

FIG. 12 is a diagram illustrating another exemplary configuration of the optical sensors 10 illustrated in FIG. 11. As illustrated in FIG. 12, the detection device 1 may have a configuration in which the four optical sensors 10 having equal areas of the light-receiving areas 10A are arranged along the circumferential direction 200C of the housing 200. In this case, the detection device 1 is provided with light-blocking layers 10B, 10C, and 10D that each covers a portion of the light-receiving area 10A, thereby adjusting the exposed areas of the light-receiving areas 10A of the optical sensors 10. The light-blocking layers 10B, 10C, and 10D are resin layers that block a wavelength band that can be received by the optical sensors 10. The light-blocking layer 10D is formed on the surface of the light-receiving area 10A using a low-polymerized resin (such as BM). The light-blocking layer 10B blocks light from reaching approximately ¼ of the light-receiving area 10A of the optical sensor 10-2. The light-blocking layer 10C blocks light from reaching approximately ½ of the light-receiving area 10A of the optical sensor 10-3. The light-blocking layer 10D blocks light from reaching approximately ¾ of the light-receiving area 10A of the optical sensor 10-3.

Thus, the detection device 1 uses the optical sensors 10 of the same size and the light-blocking layers 10B, 10C, and 10D of different sizes, whereby the sizes, that is, the sensitivities, of the light-receiving areas 10A of the optical sensors 10 vary. This configuration allows the optical sensors 10 of the detection device 1 to be commonized, and can thereby reduce costs.

Figure 13:
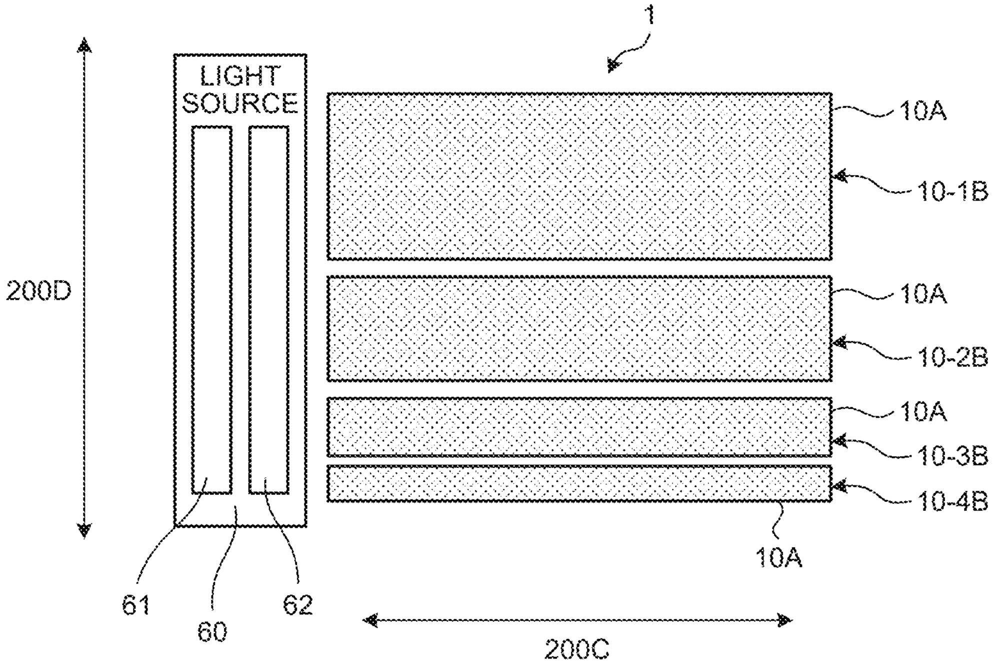
FIG. 13 is a view for explaining another exemplary arrangement relation of the optical sensors with the light sources.

FIG. 13 is a view for explaining another exemplary arrangement relation of the optical sensors 10 with the light source 60. As illustrated in FIG. 13, in the detection device 1, the optical sensors 10 may have the same length in the circumferential direction 200C of the housing 200. That is, the detection device 1 includes four optical sensors 10-1B, 10-2B, 10-3B, and 10-4B. The optical sensors 10-1B, 10-2B, 10-3B, and 10-4B are equal in length in the circumferential direction 200C of the housing 200 and different in length in the width direction 200D of the housing 200. That is, the optical sensors 10-1B, 10-2B, 10-3B, and 10-4B each have a different area of the light-receiving areas 10A. This configuration can equalize the distances from the light source 60 to the optical sensors 10-1B, 10-2B, 10-3B, and 10-4B in the detection device 1, so that the detection accuracy of the optical sensors 10 can be improved.

Figure 14:
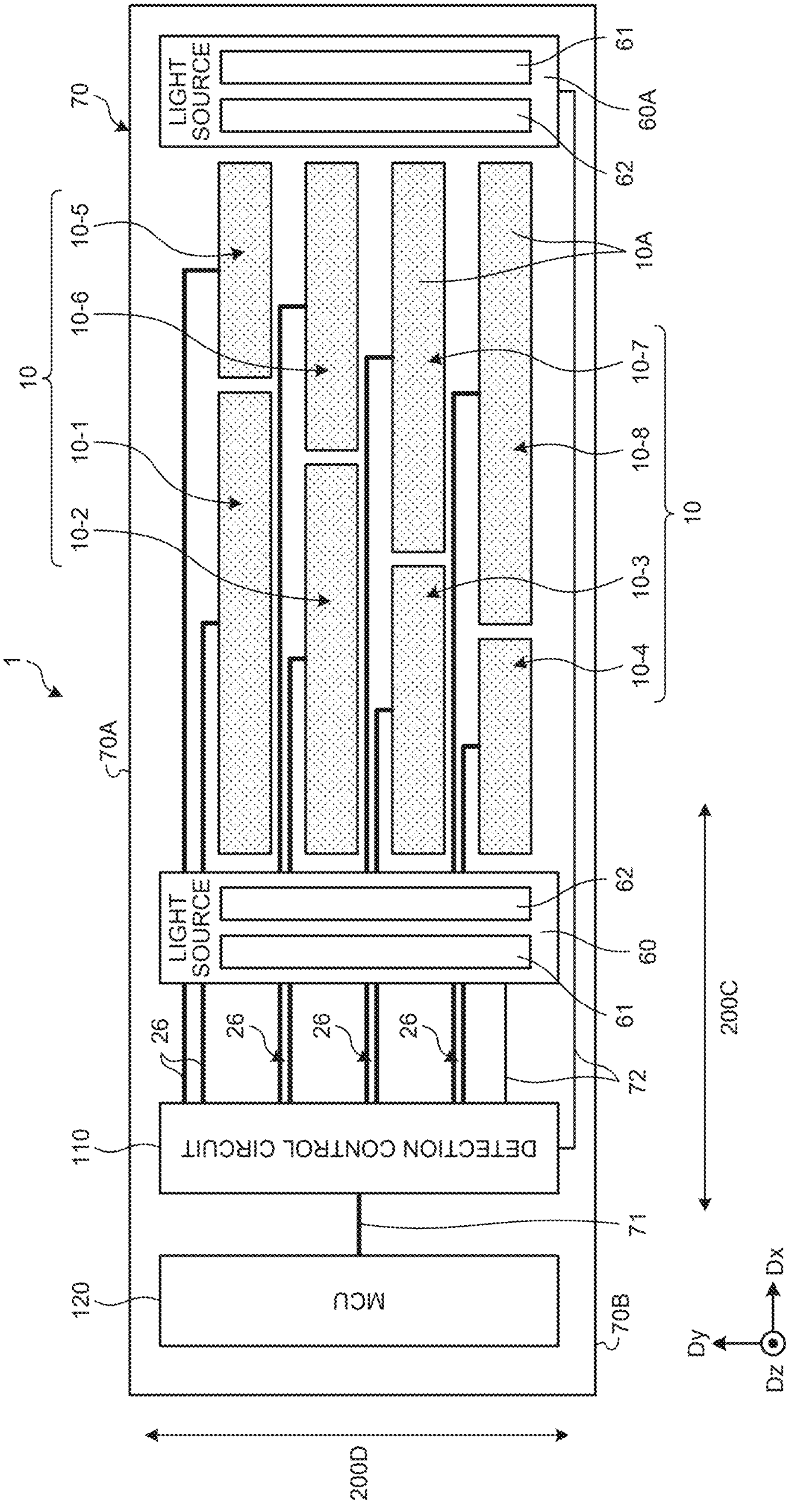
FIG. 14 is a schematic plan view illustrating an exemplary configuration of the optical sensors and the light sources of the detection device according to another modification of the embodiment.

FIG. 14 is a schematic plan view illustrating an exemplary configuration of the optical sensors 10 and the light sources 60 of the detection device 1 according to another modification of the embodiment. As illustrated in FIG. 14, the detection device 1 can be configured with eight optical sensors 10. In the example illustrated in FIG. 14, the detection device 1 includes optical sensors 10-1, 10-2, 10-3, 10-4, 10-5, 10-6, 10-7, and 10-8, which are provided on the flexible printed circuit board 70. The arrangement of the optical sensors 10-1, 10-2, 10-3, and 10-4 is the same as that of the optical sensors 10-1, 10-2, 10-3, and 10-4 illustrated in FIG. 3 explained above.

The optical sensors 10-5, 10-6, 10-7, and 10-8 are arranged in the width direction 200D of the housing 200 and have different lengths in the circumferential direction 200C orthogonal to the width direction 200D. The optical sensors 10-5, 10-6, 10-7, and 10-8 have lengths in the circumferential direction 200C of the housing 200 gradually increasing from the one end 70A toward the other end 70B of the flexible printed circuit board 70. The optical sensors 10-1, 10-2, 10-3, and 10-4 and their corresponding optical sensors 10-5, 10-6, 10-7, and 10-8 are arranged in a plurality of lines arranged in the width direction 200D of the housing 200 such that the lengths in the circumferential direction 200C differ from one another. Specifically, the optical sensors 10-5, 10-6, 10-7, and 10-8 are arranged respectively adjacent to the optical sensors 10-1, 10-2, 10-3, and 10-4 in the circumferential direction 200C on a one-to-one basis, such that two optical sensors 10 adjacent in the circumferential direction 200C have different lengths. The arrangement order of the optical sensors 10-5, 10-6, 10-7, and 10-8 in the width direction 200D from the one end 70A and the arrangement order of the optical sensors 10-1, 10-2, 10-3, and 10-4 in the width direction 200D from the one end 70A are reversed in terms of the length in the circumferential direction 200C. In other words, the arrangement of the optical sensors 10-5, 10-6, 10-7, and 10-8 in the width direction 200D and the arrangement of the optical sensors 10-1, 10-2, 10-3, and 10-4 in the width direction 200D have a symmetrical relation in terms of the length in the circumferential direction 200C. In the present embodiment, the optical sensor 10-5 has the same length as the optical sensor 10-4. The optical sensor 10-6 has the same length as the optical sensor 10-3. The optical sensor 10-7 has the same length as the optical sensor 10-2. The optical sensor 10-8 has the same length as the optical sensor 10-1.

In the detection device 1, the light source 60A is located near the optical sensors 10-5, 10-6, 10-7, and 10-8. The light source 60A includes the first light source 61 and the second light source 62. The light source 60A is electrically coupled to the detection control circuit 110 via the wiring 72. The second light source 62 is located closer to the optical sensors 10-5, 10-6, 10-7, and 10-8 than the first light source 61.

As illustrated in FIG. 10 explained above, the detection device 1 measures the external light intensity (Step S101). For example, the detection device 1 drives any one or at least one of the optical sensors 10-1, 10-2, 10-3, 10-4, 10-5, 10-6, 10-7, and 10-8, acquires the waveform data detected by the driven optical sensor or sensors 10, and measures the external light intensity based on the waveform data.

The detection device 1 sets the luminance of the light source according to the external light intensity (Step S102). For example, the detection device 1 identifies the light source luminance corresponding to the external light intensity using the external light intensity measured at Step S101 and the table data 500 (refer to FIG. 6) described above, and sets the light source luminance as the luminance of the light sources 60 and 60A.

The detection device 1 detects light using all the optical sensors 10 (Step S103). For example, the detection device 1 turns on the first light source 61 or the second light source 62 of the light sources 60 and 60A at the set luminance, acquires the waveform data detected by the detection circuit 112 for each of the optical sensors 10-1, 10-2, 10-3, 10-4, 10-5, 10-6, 10-7, and 10-8, and stores the acquired waveform data in the storage circuit 122.

The detection device 1 selects the optical sensor 10 that satisfies the selection condition from all the optical sensors 10 (Step S104). For example, the detection device 1 identifies the waveform data having the waveform amplitude satisfying the selection condition from the plurality of pieces of waveform data of the optical sensors 10-1, 10-2, 10-3, 10-4, 10-5, 10-6, 10-7, and 10-8. For example, the detection device 1 identifies the waveform data having the largest waveform amplitude, the waveform data having the largest peak-to-peak distance, or the like from a plurality of pieces of the waveform data for each of the optical sensors 10. Alternatively, the detection device 1 calculates the average value of the predetermined number of amplitudes of the waveform indicated by the waveform data for each piece of the waveform data of the optical sensors 10-1, 10-2, 10-3, 10-4, 10-5, 10-6, 10-7, and 10-8, and identifies the waveform data having the largest average value. The detection device 1 then selects the optical sensor 10 that has detected the identified waveform data as the optical sensor 10 that satisfies the selection condition.

The detection device 1 outputs the data of the selected optical sensor 10 (Step S105). For example, the detection device 1 requests the display apparatus, the smartphone, or the like to output the waveform data selected at Step S104. Thus, the detection device 1 can output the waveform data less affected by the external light.

The detection device 1 executes the predetermined procedure illustrated in FIG. 10 so as to turn on the first light sources 61 of the light sources 60 and 60A and acquire and output the waveform data, and then, executes the predetermined procedure illustrated in FIG. 10 so as to turn on the second light sources 62 of the light sources 60 and 60A and acquire and output the waveform data. In this way, the detection device 1 alternately turns on the first and the second light sources 61 and 62, and acquires the signals having wavelength components of the respective light sources in a time-division manner. The detection device 1 then performs the process to calculate the blood oxygen saturation level ($SpO_2$) based on the ratio in hemoglobin absorbance at two wavelengths (red light/infrared light). The detection device 1 displays the biometric information including the blood oxygen saturation level and other information on the display device or transmit it via the communication device.

Thus, arranging the eight optical sensors 10 are arranged along the circumferential direction 200C of the housing 200 in the detection device 1, whereby the detection area of the optical sensors 10 is further expanded. Since this configuration allows the detection device 1 to acquire the waveform data less affected by the external light while being worn on the finger Fg, the measurement accuracy can be improved.

The components in the embodiment described above can be combined as appropriate. Other operational advantages accruing from the aspects described in the embodiment that are obvious from the description herein, or that are conceivable as appropriate by those skilled in the art will naturally be understood as accruing from the present disclosure.

What is claimed is:

1. A detection device comprising:

a light source;

a plurality of optical sensors that are arranged so as to be capable of receiving light of the light source and have light-receiving areas different in size;

a detection circuit that is electrically coupled to each of the optical sensors and configured to detect waveform data that allows an amount of received light of each of the optical sensors to be identified; and a control circuit configured to select at least one piece of the waveform data having waveform amplitude that satisfies a selection condition from a plurality of pieces of the waveform data detected by the optical sensors, wherein the control circuit is configured to determine and select the waveform data that has a largest average value of a plurality of amplitudes of waveforms indicated by the waveform data, from among the pieces of the waveform data detected by the optical sensors.

2. The detection device according to claim 1, further comprising an external light detection circuit configured to detect an external light intensity, wherein the light source is configured to emit a larger amount of light as the external light intensity increases.

3. The detection device according to claim 1, wherein the control circuit is configured to select the waveform data in accordance with a predetermined priority order when a plurality of the average values are the same.

4. The detection device according to claim 3, wherein the control circuit is configured to select the waveform data of the optical sensor having a smaller area of the light-receiving area when a plurality of the average values are the same.

5. The detection device according to claim 4, wherein the external light detection circuit is configured to detect the external light intensity based on the waveform data of any one of the optical sensors.

6. The detection device according to claim 5, wherein the external light detection circuit is configured to use the waveform data of the optical sensor having a largest size of the light-receiving area among the optical sensors.

7. The detection device according to claim 6, wherein the light source is configured not to emit light when detecting the external light.

8. The detection device according to claim 7, wherein the light-receiving areas of the optical sensors have the same area, and light-blocking layers covering the light-receiving areas have different areas.

9. The detection device according to claim 7, wherein the light-receiving areas of the optical sensors have different sizes in at least one of first and second directions.

10. The detection device according to claim 1, wherein the optical sensors are arranged in the first direction and have different lengths in the second direction intersecting the first direction.

11. The detection device according to claim 10, wherein the optical sensors are arranged such that the optical sensors having different lengths in the first direction are arranged adjacent in the second direction and the optical sensors having different lengths in the second direction are arranged adjacent in the first direction.

12. The detection device according to claim 1, wherein the light source is configured to emit any one of infrared light, red light, and green light.

13. The detection device according to claim 1, wherein the light source is configured to emit red light and either one of infrared light and green light.

* * * * *